United States Patent [19]

Bingel

[11] Patent Number: 5,739,376
[45] Date of Patent: Apr. 14, 1998

[54] FULLERENE DERIVATIVES, METHODS OF PREPARING THEM AND THEIR USE

[75] Inventor: Carsten Bingel, Frankfurt am Main, Germany

[73] Assignee: Hoechst Aktiengesellschaft, Frankfurt, Germany

[21] Appl. No.: 535,163

[22] PCT Filed: Apr. 7, 1994

[86] PCT No.: PCT/EP94/01079
§ 371 Date: Oct. 20, 1995
§ 102(e) Date: Oct. 20, 1995

[87] PCT Pub. No.: WO94/25424
PCT Pub. Date: Nov. 10, 1994

[30] Foreign Application Priority Data

Apr. 24, 1993 [DE] Germany ............ 43 13 481.5

[51] Int. Cl.$^6$ .................. C07C 69/76
[52] U.S. Cl. .................. 560/51; 560/54; 560/39; 560/127; 562/509; 562/459; 549/274; 549/454; 568/329; 540/467; 564/47

[58] Field of Search .................. 560/127, 51, 54, 560/39; 549/274, 454; 562/509, 459; 568/329; 540/467; 564/47

[56] References Cited

PUBLICATIONS

Bingel, Carsten, "Cyclopropanierung von Fullerenen", *Chem. Ber.* 1993, 126:1957–1959.

*Primary Examiner*—Samuel Barts
*Attorney, Agent, or Firm*—Frommer Lawrence & Haug LLP

[57] ABSTRACT

Fullerene derivatives, methods of preparing the same and methods of using the same, wherein the fullerene derivatives are of the formula I

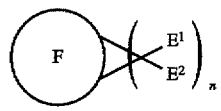

I

5 Claims, No Drawings

FULLERENE DERIVATIVES, METHODS OF PREPARING THEM AND THEIR USE

This application is a 371 of application PCT/EP/01079 filed Apr. 7, 1994.

Fullerenes are cage-like carbon allotropes of the formula $C_{(20+2m)}$ (where m=a natural number). They contain twelve five-membered rings and also any number, but at least two, six-membered rings of carbon atoms. Although this class of compound was discovered only in 1985 by Kroto and Smalley (Nature, 1985, 318, 162) and Krätschmer and Huffman only reported the preparation of macroscopic amounts of $C_{60}$ in 1990 (Nature 1990, 347, 354), such compounds have very quickly attracted wide interest and within a very short time have become the subject of numerous research studies (see, for example, G. S. Hammond, V. J. Kuck (Editors), Fullerenes, American Chemical Society, Washington D.C. 1992 and Accounts of Chemical Research, March edition 1992).

Since a high potential is expected of this class of substances, for example in the fields of optoelectronics and research on active compounds, efforts have already been made to form derivatives, in particular of $C_{60}$ (see, for example, H. Schwarz, Angew. Chem. 1992, 104, 301 and F. Wudl et al. in G. S. Hammond, V. J. Kuck (Editors), Fullerenes, American Chemical Society, Washington D.C. 1992 and Accounts of Chemical Research, March edition 1992).

Some experiments on forming derivatives succeeded in isolating defined products. Examples are the reactions of fullerenes in 1,3 dipolar cycloadditions with diazo compounds (e.g. F. Wudl et al., Acc. Chem. Res. 1992, 25, 157) and also in [2+1] carbene additions with nucleophilic glycosylidenecarbenes (e.g. A. Vasella et al., Angew. Chem. 1992, 104, 1383).

Further examples are the addition of nucleophiles such as organolithium and organomagnesium compounds (e.g. A. Hirsch et al., Angew. Chem. 1992, 104, 808).

It was desirable to synthesize fullerene derivatives containing structural units having those functional groups which are known to have applications in the field of research on active compounds, which can also be utilized for the construction of new polymer materials and which improve the physical properties, such as solubility or polarity, of the fullerene derivatives.

It has long been known that 1,3-dicarbonyl compounds such as malonic esters and β-ketoesters have proven useful in the synthesis of active compounds (e.g. Organikum 16, intended edition 1986, pages 393, 413, 414).

The linking of acid C–H compounds, such as malonic esters or β-ketoesters, with activated olefins is known as the Michael edition (e.g. Organikum 16, intended edition 1986, page 507). It has now been found that well-defined fullerene derivatives can be obtained by reacting fullerenes, for example, with the anions of 2-halocarbonyl compounds.

The invention provides a fullerene derivative of the formula I

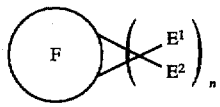

in which the symbols and indices have the following meanings:

F: is a fullerene radical of the formula $C_{(20+2m)}$ where m=20, 25, 28, 29;

$E^1$, $E^2$: are identical or different and are each COOH, COOR, CONRR$^1$, CHO, COR, CN, P(O)(OR)$_2$ and SO$_2$R, where R, R$^1$ are each a straight-chain or branched, aliphatic radical (C$_1$ to C$_{20}$) which may be unsubstituted or monosubstituted or polysubstituted by identical or different substituents, in which radical up to every third CH$_2$ unit can be replaced by O or NR$^4$, where R$^4$ is (C$_1$–C$_{20}$)-alkyl or benzyl, or a benzyl radical or phenyl radical which can be unsubstituted or substituted by from 1 to 5 substituents R, OH, OR, COOR, OCOR, SO$_3$H, SO$_2$Cl, F, Cl, Br, NO$_2$ and CN or together are

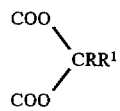

or are different from one another and are each COR, R or H, or are different from one another and are each COR/R or F/Cl/Br, where R is as defined above, or are different from one another and are each NO$_2$, R$^3$ or H, where R$^3$ is an unsubstituted, monosubstituted or polysubstituted aliphatic radical (C$_1$ to C$_{20}$);

n: is a natural number from 1 to 10+m where m=20, 25, 28, 29.

Preference is given to compounds of the formula I in which the symbols and indices have the following meanings:

F: is a fullerene radical of the formula $C_{(20+2m)}$ where m=20, 25, 28, 29, $E^1$, $E^2$: are identical or different and are each COOR, COR, P(O)(OR)$_2$, COOH, CN, where R is a straight-chain or branched, aliphatic radical (C$_1$ to C$_{20}$) which may be unsubstituted or monosubstituted or polysubstituted by identical or different substituents, in which radical up to every third CH$_2$ unit can be replaced by O or NR$^4$, where R$^4$=(C$_1$–C$_{20}$)-alkyl or benzyl, or a benzyl radical or phenyl radical which can be unsubstituted or substituted by from 1 to 3 substituents R, OH, OR, COOR, OCOR, SO$_3$H, SO$_2$Cl, F, Cl, Br, NO$_2$ and CN, or together are

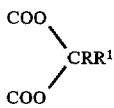

or are different from one another and are each COR, R or H, or are different from one another and are each COR/R or F/Cl/Br, n : is a natural number from 1 to 12.

Particular preference is given to compounds of the formula I in which the symbols and indices have the following meanings:

F: $C_{60}$, $C_{70}$

E1/E2: CO$_2$R$^1$/CO$_2$R$^2$; CO$_2$R$^1$/COR$^2$; CO$_2$R$^1$/CN; COAr/R$^1$ or H; COAr/R$^1$ or Cl;

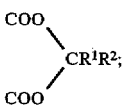

COR$^1$/COR$^2$; P(O)(OR$^1$)$_2$/P(O)(OR$^2$)$_2$; COOH/COOH; where R$^1$ and R$^2$ are identical or different and are each a straight-chain or branched alkyl radical ($C_1$ to $C_{20}$) which may be unsubstituted or monosubstituted or polysubstituted by identical or different substituents, in which radical every third $CH_2$ unit can be replaced by O or $NR^4$, where $R^4=(C_1-C20)$-alkyl or benzyl, or a benzyl radical or phenyl radical which can be unsubstituted or substituted by from 1 to 3 substituents OH, OMe, $CO_2R^1$, $OOCR^1$, $SO_3H$, $SO_2Cl$, F, Cl, Br, $NO_2$ and CN, and Ar is a phenyl radical which can likewise be substituted by from 1 to 3 substituents OH, OMe, Me, $CO_2R^1$, $OCOR^1$, $SO_3H$, $SO_2Cl$, F, Cl, Br, $NO_2$ and CN or can be substituted by a straight-chain or branched aliphatic radical ($C_1-C_{20}$), preferably $C_1-C_{10}$, which may be unsubstituted or monosubstituted or disubstituted by identical or different substituents $COOR^5$, $CONHR^5$, $CONR_2^5$, $CONH_2$, $CONR^6$, COOH, OH or $OCOR^5$, $COOAr$, $COOCH_2Ar$, where $R^5=$

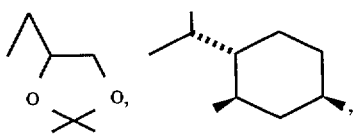

$C_1-C_6$-alkyl, hydroxy-($C_1-C_6$)-alkyl, carboxy ($C_1-C_6$) -alkyl or ($C_1-C_3$)-alkylcarboxyl-($C_1-C_6$)-alkyl;

$R^6=C_{11}-C_{17}$-alkylene in which up to every 3rd $CH_2$ unit can be replaced by O and which together with the amide nitrogen forms a $C_{12}-C_{18}$ ring, and Ar is as defined above;

n: is a natural number from 1 to 6.

Very particular preference is given to compounds of the formula I in which the symbols and indices have the following meanings:

F: $C_{60}$, $C_{70}$ $E^1/E^2$: $CO_2Alkyl^1/CO_2Alkyl^1$; $CO_2Alkyl^1/COAlkyl^2$; $COAr/Ar$; $COAr/Alkyl^1$; $COAr/H$ where $Alkyl^1$, $Alkyl^2$ are each a straight-chain or branched alkyl radical having from 1 to 10 carbon atoms in which up to every third $CH_2$ unit can be replaced by O, and Ar is a phenyl group which can be substituted by a straight-chain or branched aliphatic radical ($C_1-C_6$) which may be unsubstituted or monosubstituted or disubstituted by identical or different substituents $COOR^5$, $CONHR^5$, $CONR_2^5$, $CONR^6$, COOH, OH or $OCOR^5$, where $R^5$ and $R^6$ are as defined above, n: is 1 or 2.

The straight-chain or branched aliphatic radical ($C_1-C_{20}$) R, $R^1$ can be, for example, preferably monosubstituted or disubstituted by identical or different substituents OH, COOH, COOAr, $CONR_2^5$, $CONR^6$, $OCOR^5$, $COOCH_2Ar$, $CONHCH_2Ar$, $CONHAr$, $CONHR^5$, $COOR^5$, halogen, $CONH_2$, $COCH_2Ar$, COAr, CO ($C_1-C_6$)-alkyl or CHO, where Ar, $R^5$ and $R^6$ are as defined above.

The compounds of the invention having the formula I are prepared, for example, by cyclopropanation of fullerene with an α-halo-CH-acid compound in the presence of a suitable base (e.g. L. L. McCoy, J. Amer. Chem. Soc. 1958, 80, 6568) or by reaction of suitably functionalized cyclopropanated fullerene derivatives by known methods, with care having to be taken to ensure that the reagents used do not react with the electrophilic fullerene radical.

The invention further provides the following process for preparing fullerene derivatives of the formula I

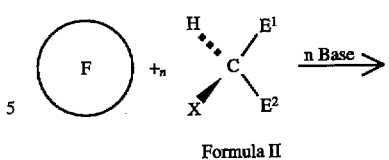

Formula II

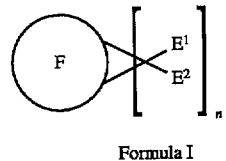

Formula I where

F is a fullerene radical of the formula $C_{(20+2m)}$ where m=20, 25, 28, 29, $E^1$ and $E^2$ are identical or different and are each COOH, COOR, $CONRR^1$, CHO, COR, CN, $P(O)(OR)_2$ and $SO_2R$, where R, $R^1$ are each a straight-chain or branched aliphatic radical ($C_1$ to C20) which may be unsubstituted or monosubstituted or polysubstituted by identical or different substituents, in which radical up to every third $CH_2$ unit can be replaced by O or $NR^4$, where $R^4$ is ($C_1-C_{20}$)-alkyl or benzyl, or a benzyl radical or phenyl radical which can be unsubstituted or substituted by from 1 to 5 substituents R, OH, OR, COOR, OCOR, $SO_3H$, $SO_2Cl$, F, Cl, Br, $NO_2$ and CN or together are

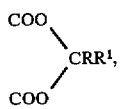

or are different from one another and are each COR, R or H, or are different from one another and are each COR/R or F/Cl/Br, or are different from one another and are each $NO_2$, $R^3$ or H, where $R^3$ can be an unsubstituted, monosubstituted or polysubstituted aliphatic radical ($C_1$ to $C_{20}$), X is —Cl, —Br, —I, —$OSO_2Ar$, $OSO_2CF_3$, $OSO_2C_4F_9$, base: is alkali metal hydride, alkali metal hydroxide, alkoxide, amide, amine, guanidine n is a natural number from 1 to 10+m where m=20, 25, 28, 29.

Preference is given to a process for preparing compounds of the formula I, in which a fullerene of the formula $C_{(20+2m)}$ (m=20, 25, 28, 29) is reacted in an aprotic organic solvent such as toluene, chlorobenzene, benzene, $CH_2Cl_2$ with compounds of the formula II in the presence of suitable bases in a temperature range from −78° C. to 180° C., preferably from 0° to 110° C. and in appropriate cases at room temperature (20°–30° C.).

The selection of the base depends on the pKa and the sensitivity of the CH acid compound to the base used.

The preparation of compounds of the formula I where n=1 is carried out at approximate stoichiometry of the starting compounds, preferably in a temperature range from −78° C. to +50° C., particularly preferably at from 0° C. to 50° C. A higher degree of substitution and thus a greater value for n is achieved by using excess CH acid compound of the formula II and a sufficient amount of base and accelerating the reaction by heating, if appropriate, to above 100° C.

However, the compounds of the formula I obtainable by the process of the invention can also be prepared in well-defined form by means of subsequent reactions by, for example, an ester of the formula I being saponified to give the corresponding acid of the formula I or an alcohol of the formula I being reacted with an acid to give an ester of the formula I or an ester of the formula I being reacted with an amine to give the corresponding amide of the formula I.

The fullerene used is preferably pure $C_{60}$ and/or $C_{70}$, but it is also possible to use crude fullerenes containing a mixture of $C_{60}$ and $C_{70}$ as main components. However, all other conceivable fullerenes or fullerene derivatives can also be used.

The fullerenes can be obtained by preparation of fullerene black in an electric arc process with subsequent extraction using a nonpolar organic solvent (crude fullerene), as described, for example, in WO 92/09279. The further fine separation can be carried out by column chromatography.

Some of the fullerenes used are also commercial products.

The cyclopropanation reagents used can be, on the one hand, commercial α-halo CH acid compounds or the compounds of the formula II which are used can be obtained by methods known to the chemist, such as the halogenation of CH acid compounds or, for example, the Friedel-Crafts acylation of substituted aromatics using bromoacetyl halides. Ester and amide functions are obtained from the desired carboxylic acids and alcohols or amines by known methods.

The compounds of the invention having the formula I are used, for example, in optoelectronic components.

The invention is illustrated by the examples.

Index of Abbreviations $CDCl_3$: deuterotrichloromethane
$CD_2Cl_2$: dideuterodichloromethane
$CS_2$: carbon disulfide
DBU: 1,8-diazobicyclo[5.4.0]undec-7-ene
DMAP: 4-dimethylaminopyridine
d: doublet (NMR) or day(s) (indication of time)
$Et_2O$: diethyl ether
HPLC: high-pressure liquid chromatography
h: hours
MS (FAB): mass spectrometry (fast atom bombardment)
m: medium (IR) or multipier (NMR)
NaH: sodium hydride
q or quart: quartet (NMR)
quint: quintet (NMR)
$R_f$: ratio of fronts in thin-layer chromatography
S: singlet (NMR) or strong (IR)
$SiO_2$: silica gel for chromatographic purposes
t: triplet (NMR)
W: weak (IR)

EXAMPLE 1

In a 250 ml nitrogen flask, 435 mg (0.60 mmol) of $C_{60}$ were dissolved in 200 ml of toluene. 0.144 g (6.0 mmol) of NaH were introduced and 0.216 g (0.90 mmol) of diethyl bromomalonate was added thereto. The suspension was stirred for 6.5 h at room temperature, quenched with 8 drops of 1 molar $H_2SO_4$ solution, dried with magnesium sulfate and filtered. According to HPLC, 65% of the $C_{60}$ used had been reacted. Chromatography over silica gel (0.063–0.2 mm) using toluene/hexane 1:1 and toluene gave

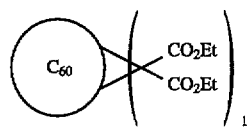

in microcrystalline form (0.238 g, 45%).

$R_f(SiO_2;$ toluene)=0.50 MS (FAB): 878 ($M^+$) IR (on KBr): ν [$cm^{-1}$]=2979(w), 1745(C=O), 1428($C_{60}$), 1295 (m), 1266 (m), 1234 (s), 1206 (m), 1186 ($C_{60}$), 1095 (m), 1061 (w). $^1$H-NMR (360 MHz, $CDCl_3$): δ=4.57 (q, J=7.13 Hz, 4H), 1.49 (t, J=7.13 Hz, 6H). $^{13}$C-NMR (100 MHz, $CDCl_3$) δ=163.55, 145.35, 145.26, 145.20, 145.18, 144.88, 144.69, 144.67, 144.60, 143.88, 143.08, 143.01, 142.99, 142.21, 141.92, 140.94, 139.03, 71.64, 63.37, 52.26, 14.22. Analysis calc. for $C_{67}H_{10}O_4$: C: 91.6% H: 1.1% found C: 92.4% H: 1.4%

EXAMPLE 2

The procedure of Example 1 was repeated, using 0.7 g (0.98 mmol) of $C_{60}$, 0.29 g (1.2 mmol) of diethyl bromomalonate and 0.23 g (9.6 mmol) of NaH in the reaction to give, after workup and chromatography over silica gel (0.063–0.2 mm), 0.33 g (39%) of monoadduct and

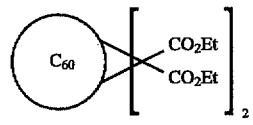

(0.048 g, 4.7%). According to TLC, more than 1 isomer $R_f$ ($SiO_2$; toluene)=from 0.19 to 0.24 MS (FAB): 1036 ($M^+$)

EXAMPLE 3

Under protective gas, 471 mg (0.654 mmol) of $C_{60}$ in 200 ml of toluene were admixed with 207 mg (0.981 mmol) of dimethyl bromomalonate and 125 mg (0.821 mmol) of DBU and stirred for 4 h at room temperature. The reaction mixture was filtered and the solution was evaporated to a volume of 60 ml. According to HPLC 69% of $C_{60}$ were reacted. Chromatography over $SiO_2$ (0.063–0.2 mm) using toluene/i-hexane 1:1, 2:1 and 3:1 gave

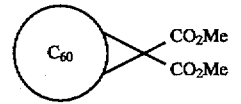

in microcrystalline form (249.3 mg, 44%) and in addition 114 mg (24%) of $C_{60}$ were recovered. $R_f(SiO_2$; toluene)= 0.37 (toluene) MS (FAB): 850 ($M^-$) $^1$H-NMR (360 MHz, $CDCl_3/CS_2$): δ=4.06 (s).

EXAMPLE 4

The procedure of Example 3 was repeated, with 0.137 g (0.190 mmol) of $C_{60}$ in 58 ml of toluene being reacted with 88 mg (0.19 mmol) of didecyl bromomalonate and 29 mg (0.19 mmol) of DBU and stirred for 15 h at room temperature. According to HPLC, 75% of $C_{60}$ were reacted. The reaction mixture was completely evaporated, the residue was extracted with diethyl ether (3×10 ml), the ether solution was filtered through silica gel and, after removal of the ether, chromatographed over $SiO_2$ (0.063–0.2 mm) using toluene/i-hexane 1:1 and 2:1.

This gave

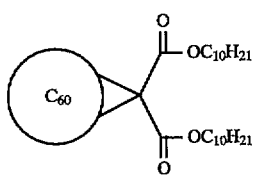

as a brown viscous oil (66 mg, 31%). $R_f(SiO_2$; toluene/i-hexane 1:1)=0.4 MS (FAB): 1102 (M⁻). ¹H-NMR (360 MHz, CDCl₃): δ=4.47 (t, J=6.5 Hz, 4H), 1.82 (m, 4H), 1.43 (m, 4H), 1.26 (m, 24H), 0.82 (t, J=6.0 Hz, 6H). ¹³C-NMR (100 MHz, CDCl₃): δ=163.65, 145.39, 145.24, 145.17, 145.16, 144.86, 144.67, 144.65, 144.59, 143.87, 143.06, 143.00, 142.97, 142.19, 141.90, 140.93, 138.99, 71.70, 67.46, 52.47, 31.88, 29.61, 29.56, 29.33, 29.24, 28.61, 25.99, 22.68, 14.12

EXAMPLE 5

The procedure of Example 3 was repeated, with 943 mg (1.31 mmol) of $C_{60}$ in 400 ml of toluene being reacted with 506 mg (1.31 mmol) of di(2-(2-methoxyethoxy)ethyl) bromomalonate and 199 mg (1.31 mmol) of DBU. After a reaction time of 18 h at room temperature, the reaction mixture was filtered and chromatographed over 50 g of silica gel (0.063–0.2 m). $C_{60}$ was eluted with toluene and the monoaddition product was eluted with 800 ml of toluene/diethyl ether 1:1. This gave 504 mg (37% based on $C_{60}$ used) of monaddition product

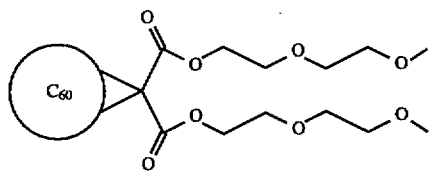

$R_f(SiO_2$; toluene/$Et_2O$ 1:1)=0.21 MS(FAB): 1026 (M⁻, 40%), 720 (100%) ¹H-NMR (360 MHz, CDCl₃): δ=4.64 (m, 4H), 3.87 (m, 4H), 3.67 (m, 4H), 3.53 (m, 4H), 3.36 (s, 6H).

EXAMPLE 6

The procedure of Example 3 was repeated, with 236 mg (0.33 mmol) of $C_{60}$ in 100 ml of toluene being reacted with 50 mg (0.33 mmol) of DBU and a solution of 74 mg (0.33 mmol) of 2,2-dimethyl-5-bromo-4,6-diketo-1,3-dioxane in 2 ml of methylene chloride. After a reaction time of 18 h at room temperature, the reaction mixture was filtered, evaporated to half its volume and chromatographed over 100 g of silica gel (0.063–0.2 mm). $C_{60}$ was eluted with 300 ml of toluene/i-hexane 1:1 and the monoaddition product was eluted with 350 ml of toluene. After removal of the solvent, the black microcrystalline monoaddition product was washed with pentane and diethyl ether and dried in vacuo. This gave 60.2 mg (21%) of $C_{60}$ $R_f(SiO_2$; toluene)=0.40 MS (FAB): 892 (M⊖, 20%), 804 (M⊖-acetone, 25%), 760 (M⊖-acetone-$CO_2$, 55%), 720 (100%). ¹H-NMR (360 MHz, CDCl₃): δ: 2.18 (s) ¹³C-NMR (100 MHz, CDCl₂): δ=160.11(C=O), 145.90, 145.66, 145.62 (2C), 145.42, 145.15, 145.01(2C), 145.00, 144.40, 143.82, 143.57 (2C), 143.50, 143.44, 142.64, 141.89, 141.75, 141.36, 106.34, 71.69, 44.74, 28.33

EXAMPLE 7

The procedure of Example 3 was repeated, with 123 mg (0.17 mmol) of $C_{60}$ in 50 ml of toluene being reacted with 51 mg (0.17 mmol) of di-tert-butyl bromomalonate and 26 mg (0.17 mmol) of DBU. After a reaction time of 4 h at room temperature, the reaction mixture was filtered, evaporated to a volume of 20 ml and chromatographed over 50 g of silica gel (0.063–0.2 mm). Using the eluant mixture toluene/i-hexane 1:1.5, $C_{60}$ and the monoaddition product were eluted and separated from the polyaddition products. After removal of the solvent, the residue was taken up in methylene chloride, with only small amounts of $C_{60}$ being extracted together with the monoaddition product, and the methylene chloride solution was evaporated to 5 ml. The chromatographic separation over 80 g of silica gel (0.063–0.2 mm) using toluene/i-hexane 1:2 and toluene gave, after washing with pentane and diethyl ether and drying in vacuo, 60 mg (37%) of monoaddition adduct.

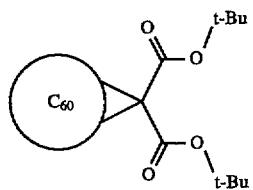

$R_f(SiO_2$; toluene)=0.58 MS(FAB): 934 (M⊖, 75%), 734 (90%), 720 (100%). ¹H-NMR (360 MHz, CDCl₃): δ=1.68 (s)

EXAMPLE 8

In a 100 ml two-neck flask, 50 mg (0.054 mmol) of bis(t-butoxycarbonyl)methanofullerene from Example 7 were dissolved under an argon atmosphere in 30 ml of chloroform and achnixed with 650 mg (6.7 mmol) of methanesulfonic acid. After about 2 h, a precipitate formed. After 24 h, the solution over the precipitate was colorless. The precipitate was separated off from the solvent and washed twice with ether to remove excess acid. Drying in vacuo gave 19 mg (43%) of

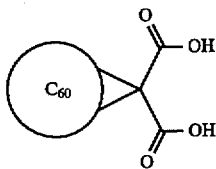

MS(FAB): 822 (M⊖, 30%), 778 (M⊖-$CO_2$, 30%), 734 (M⊖-2 $CO_2$ 100%), 720 (70%).

EXAMPLE 9

236 mg (0.328 mmol) of fullerene $C_{60}$ in 100 ml of toluene were placed in a 250 ml nitrogen flask and 102 mg (0.67 mmol) of DBU and 62 mg (0.412 mmol) of methyl 2-chloroacetate were injected in. After 2 h, the reaction mixture was filtered.

According to HPLC, 80% of the $C_{60}$ used were reacted. Chromatography over silica gel (0.063–0.2 mm) using toluene/i-hexane (1:1) and toluene gave

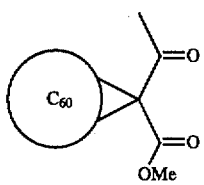

in microcrystalline form (775 mg, 27%). R$_f$(SiO$_2$; toluene) =0.44 MS (FAB): 834 (M$^-$) IR (on KBr): ν [cm$^{-1}$]=2996 (w), 2943 (w), 1756 (C=O), 1718 (C=O), 1428 (C$_{60}$), 1356 (w), 1265 (w), 1231 (s), 1200 (m), 1186 (C$_{60}$). $^1$H-NMR (360 MHz, CDCl$_3$): δ=4.10 (s, 3H), 2.87 (s, 3H). $^{13}$C-NMR (100 MHz, CDCl$_3$): δ=193.64, 164.45, 145.44, 145.28, 145.28, 145.25, 145.21, 145.20, 145.08, 144.87, 144.75, 144.75, 144.74, 144.74, 144.69, 144.61, 144.61, 143.88, 143.84, 143.17, 143.12, 143.07, 143.06, 143.06, 142.98, 142.24, 142.24, 141.93, 141.90, 141.08, 141.01, 139.45, 138.03, 72.33, 54.09, no signal for methoxy C, 28.84. Analysis calc. for C$_{65}$H$_6$O$_3$: C: 93.53 H: 0.72 found C: 93.4 H: 0.8

EXAMPLE 10

The procedure of Example 9 was repeated, with 0.471 g (0.654 mmol) of C$_{60}$ in 200 ml of toluene being reacted with 108 mg (0.656 mmol) of ethyl 2-chloroacetate and 99.5 mg (0.654 mmol) of DBU and stirred for 2.5 h at room temperature. The reaction mixture was filtered and the solution was evaporated to from 60 to 70 ml. According to HPLC, only 24% of C$_{60}$ were reacted. Chromatography over SiO$_2$ (0.063–0.2 mm) using toluene/i-hexane 1:1 and toluene, carried out twice, gave

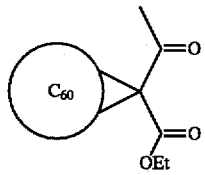

in microcrystalline form (111.5 mg, 20%) and, in addition, 280 mg (59%) of C60 were recovered. R$_f$(SiO$_2$; toluene)= 0.36 MS (FAB): 848 (M$^-$) $^1$H-NMR (360 MHz, CDCl$_3$): δ=4.55 (q, J=7.1 Hz, 2H), 2.82 (s, 3H), 1.54 (t, J=7.1 Hz, 3H).

EXAMPLE 11

151 mg (0.65 mmol) of desyl chloride and 367 mg (3.27 mmol) of potassium tert-butoxide were placed in a 250 ml 2-neck flask and a solution of 236 mg (0.328 mmol) of C$_{60}$ in 100 ml of toluene was subsequently added. The mixture was stirred for 40 h at room temperature, quenched by addition of 5 drops of 1 molar H$_2$SO$_4$ solution, dried with MgSO$_4$ and filtered. According to HPLC, 60% of the C$_{60}$ used were reacted. Chromatography over silica gel (0.063–0.2 mm) using toluene/i-hexane 2:3 and toluene gave

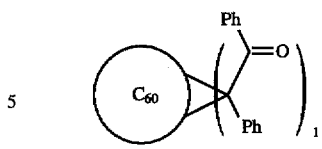

in microcrystalline form (76 mg, 25%). R$_f$(SiO$_2$, toluene/i-hexane 1:1)=0.54 MS(FAB): 914 (M$^-$) IR (on MBr): ν [cm$^{-1}$]=3051 (w), 3036 (w), 1678 (C=O), 1595 (m), 1494 (w), 1444 (m), 1427 (C$_{60}$), 1255 (m), 1187 (C$_{60}$), 697 (s). $^1$H-NMR (360 MHz, CDCl$_3$): δ=8.62 (m, 2H), 8.24 (m, 2H), 7.62–7.40 (m, 5H). $^{13}$C-NMR (100 MHz, CDCl$_3$) δ=190.57, 148.20, 146.31, 145.59, 145.29, 145.28, 145.21, 145.19, 145.19, 144.83, 144.81, 144.77, 144.74, 144.60, 144.50, 144.41, 143.92, 143.77, 143.17, 143.05, 143.01, 142.99, 142.97, 142.88, 142.34, 142.19, 142.19, 142.13, 141.13, 141.04, 138.51, 137.19, 134.22, 133.55, 132.21, 132.16, 130.34, 129.08, 128.99, 128.97, 75.78, 60.81. Analysis calc. for C$_{74}$H$_{10}$O: C: 91.6% H: 1.1% found C: 92.4% H: 1.4%

EXAMPLE 12

The procedure of Example 3 was repeated, with 471 mg (0.654 mmol) of C$_{60}$ in 200 ml of toluene being reacted with 100 mg (0.657 mmol) of DBU and 140 mg (0.657 mmol) of α-bromopropiophenone. After a reaction time of 8 days at room temperature, 52% of the C$_{60}$ have reacted according to HPLC. Chromatography over SiO$_2$ (0.063–0.2 mm) using toluene/i-hexane 1:2→2:1 and 2:3/1:1, carried out twice, gave

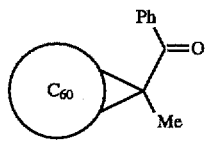

(30 mg, 5.4%). R$_f$(SiO$_2$; toluene/i-hexane 1:1)=0.31 MS (FAB): 852 (M$^-$). $^1$H-NMR (360 MHz, CDCl$_3$): δ=8.53 (m, 2 H$_{ortho}$), 7.70 (m, 1 H$_{para}$), 7.64 (m, 2 H$_{meta}$), 2.64 (s, 3H).

EXAMPLE 13

In a 250 ml nitrogen flask, 0.236 g (0.328 mmol) of C$_{60}$ were dissolved in 100 ml of toluene. 66 mg (0.331 mmol) of ω-bromoacetophenone and 0.051 g (0.334 mmol) of DBU were added and the mixture was stirred at room temperature. After 5 h, 2 drops of 2N sulfuric acid were added and the reaction mixture was dried using MgSO$_4$. After filtration and evaporation of the solution to half its volume, it was chromatographed over silica gel, after the C$_{60}$ conversion had previously been determined as 72% by HPLC. Chromatography over SiO$_2$ (0.063–0.2 mm) using toluene/i-hexane (2/3→2/1) and toluene gave

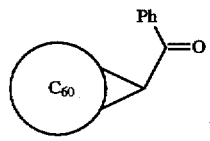

in microcrystalline form (59 mg, 21%), and additionally 81 mg of product contaminated with C$_{60}$. R$_f$(SiO$_2$, toluene)= 0.64 MS(FAB): 838 (M$^-$) IR (on KBr): ν [cm$^{-1}$]=3023 (w), 1684 (C=O), 1446 (m), (C$_{60}$), 1244 (m), 1219 (s), 1185

($C_{60}$), 1006 (s), 710 (s), 683 (s). $^1$H-NMR (360 MHz, CDCl$_3$): δ=8.46 (m, 2H), 7.75 (m, 1H), 7.67 (m, 2H), 5.64 (s, J$_{CH}$=162 Hz, 1H). $^{13}$C-NMR (100 MHz, CDCl$_3$): δ=189.69, 148.04, 146.63, 145.58, 145.39, 145.31, 145.21, 145.20, 145.09, 144.87, 144.75, 144.69, 144.66, 144.65, 144.65, 144.37, 143.96, 143.71, 143.34, 143.18, 143.05, 142.99, 142.99, 142.80, 142.49, 142.27, 142.23, 142.11, 141.22, 140.98, 139.61, 136.65, 135.95, 134.48, 129.35, 128.94, 72.30, 44.16. Analysis calc. for C$_{68}$H$_6$O: C: 97.37% H: 0.72% found C: 97.7% H: 0.8%

EXAMPLE 14

The procedure of Example 13 was repeated, with a mixture of 0.236 g (0.328 mmol) of C$_{60}$ in 100 ml of toluene, 114 mg (0.572 mmol) of ω-bromoacetophenone and 95 mg (0.62 mmol) of DBU giving 83 mg (30%) of the monoadduct and also the diadduct, as a mixture of isomers,

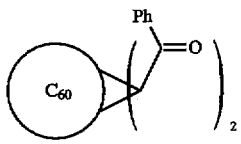

(54 mg, 17%) R$_f$: 0.47 (toluene) MS(FAB): 956 (M$^-$)

In the following examples, the reactions were carried out in an argon atmosphere, while the further workup of the individual reaction mixtures was not carried out under protective gas.

In each case, a solution of C$_{60}$ in toluene was reacted with the CH acid compound and DBU as base while stirring at room temperature. After filtration of the reaction mixtures and evaporation of the solutions to half their volume, the solutions were chromatographed over silica gel. The monoaddition products isolated were washed with diethyl ether or pentane and dried in vacuo.

EXAMPLE 15

236 mg (0.33 mol) of C$_{60}$ were stirred in 100 ml of toluene with 98 mg (0.33 mol) of ethyl 3-[4-(2-bromoacetyl)phenyl]propionate and 50 mg (0.33 mmol) of DBU for 4 h. Chromatography: 75 g of silica gel (0.063–0.2 mm); 400 ml of toluene 117 mg (38%) of

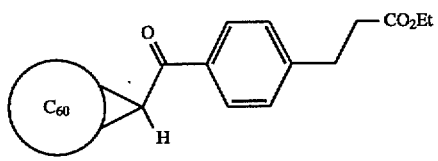

R$_f$ (SiO$_2$, toluene)=0.20 MS (FAB): 938 (M$^\ominus$, 60%), 720 (100%) $^1$H-NMR (360 MHz, CHCl$_3$): δ=8.38 (d, J=8.4 Hz, 2 H), 7.50 (d, J=8.4 Hz, 2 H), 5.61 (s, 1 H), 4.14 (q, J=7.1 Hz, 2 H), 3.10 (t, J=7.6 Hz, 2 H), 2.71 (t, J=7.6 Hz, 2 H), 1.24 (t, J=7.1 Hz, 3 H) $^{13}$C-NMR (100 MHz, CDCl$_3$): δ=189.20, 172.37, 148.06, 147.99, 146.69, 145.58, 145.39, 145.28, 145.19, 145.18, 145.07, 144.86, 144.73, 144.67, 144.64, 144.62, 144.34, 143.94, 143.70, 143.32, 143.16, 143.04, 142.98, 142.97, 142.78, 142.48, 142.26, 142.21, 142.10, 141.20, 140.96, 139.57, 136.63, 134.16, 129.34, 129.25, 72.33, 60.68, 44.19, 35.21, 31.05, 15.5

EXAMPLE 16

247 mg (0.34 mmol) of C$_{60}$ were stirred in 100 ml of toluene with 127 mg (0.34 mmol) of diethyl 2-[4-(2-bromoacetyl)benzyl]malonate and 52 mg (0.34 mmol) of DBU for 3 h. Chromatography: 70 g of silica gel (0.063–0.2 mm); 1000 ml of toluene 139 mg (40%) of

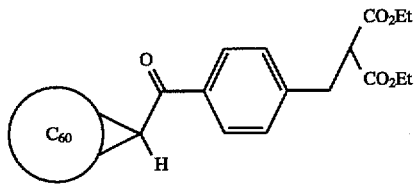

R$_f$ (SiO$_2$, toluene)=0.10 MS (FAB): 1010 (M$^\beta$, 45%), 720 (100%) $^1$H-NMR (360 MHz, CD$_2$Cl$_2$): δ=8.40 (d, J=8.4 Hz, 2 H), 7.54 (d, J=8.4 Hz, 2 H), 5.71 (s, 1 H), 4.18 (m, 4 H), 3.75 (t, J=7.7 Hz, 1 H), 3.36 (d, J=7.8 Hz, 2 H), 1.23 (t, J=7.1 Hz, 6 H). $^{13}$C-NMR (CD$_2$Cl$_2$): δ=189.1 (1C), 168.5, 148.3, 147.0, 145.7, 145.5, 145.5 (1C), 145.3, 145.2, 145.2, 145.1, 144.9 (1C), 144.8, 144.7, 144.7, 144.6, 144.4, 144.0, 143.8, 143.3, 143.2 (1C), 143.1, 143.0, 143.0, 142.9, 142.6, 142.3, 142.2, 142.2, 141.2, 141.0, 139.5, 136.8, 136.8, 134.6, 129.9, 129.2, 72.6, 61.8, 44.5, 34.7, 13.9.

EXAMPLE 17

123 mg (0.17 mmol) of C$_{60}$ were stirred in 50 ml of toluene with 49 mg (0.17 mmol) of ethyl 4-[4-(2-bromoacetyl)phenyl]butyrate and 26 mg (0.17 mmol) of DBU for 15 h. Chromatography: 40 g of silica gel (0.063–0.2 mm); 300 ml of toluene 47 mg (28%) of

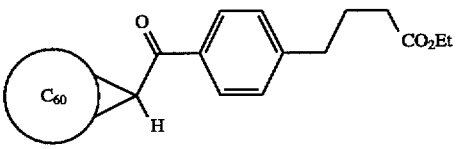

R$_f$ (SiO$_2$, toluene)=0.27 MS (FAB): 952 (M$^\ominus$, 60%), 720 (100%) $^1$H (360 MHz, CD$_2$Cl$_2$): δ=8.41 (d, J=8.3 Hz, 2 H), 7.52 (d, J=8.3 Hz, 2H), 5.72 (s, 1 H), 4.13 (quart., J=7.1 Hz, 2 H), 2.83 (t, J=7.7 Hz, 2 H), 2.40 (t, J=7.4 Hz, 2 H), 2.04 (quint, J=7.6 Hz, 2 H), 1.26 (t, J=7.1 Hz, 3H).

EXAMPLE 18

54 mg (0.63 mmol) of C$_{60}$ were heated to about 50°–60° C. in 200 ml of toluene with 350 mg (0.612 mmol) of di(4-nitrophenyl) 3-[4-(2-bromoacetyl)phenyl]glutarate and stirred together with 93 mg (0.613 mmol) of DBU for 15 hours. Chromatography: 50 g of silica gel (0.063–0.2 mm); 500 ml of toluene, 600 ml of methylene chloride 315 mg of C$_{60}$ (69% based on C$_{60}$ used) 158 mg (20%/67% based on C$_{60}$ used/C$_{60}$ reacted) of

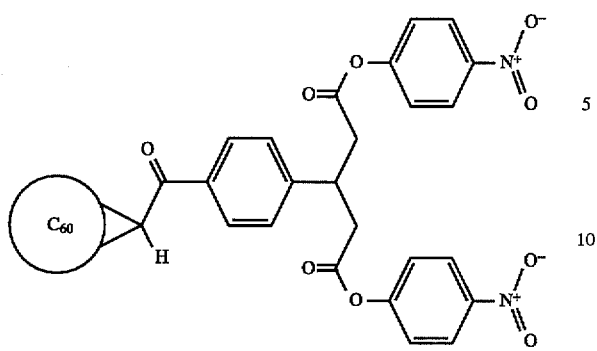

$R_f$ (SiO₂, CH₂Cl₂)=0.30 MS (FAB): 1210 (M$^\ominus$, 100%), 720 (60%) ¹H (360 MHz, CDCl₃): δ=8.49 (d, J=8.3 Hz, 2 H), 8.21 (m, 4 H), 7.68 (d, J=8.3 Hz, 2 H), 7.14 (m, 4 H), 5.61 (s, 1 H), 4.04 (quint, J=7.4 Hz, 1 H), 3.22 (d, d, $J_{AB}$=16.2 Hz, $J_{AX}$=6.8 Hz, 2 H), 3.13 (d, d, $J_{AB}$=16.2 Hz, $J_{BX}$=8.1 Hz, 2 H)

EXAMPLE 19

371 mg (0.51 mmol) of C₆₀ were stirred in 150 ml of toluene with 168 mg (0.44 mmol) of (2,2-dimethyl-1,3-dioxolan-4-yl) methyl 3-[4-(2-bromoacetyl) phenyl] propionate and 67 mg (0.44 mmol) of DBU for 15 hours. Chromatography: 25 g of silica gel (0.063–0.2 mm); 100 ml of toluene, 102 ml of toluene/ethanol 100:2, 205 ml of toluene/ethanol 100: 2.5 343 mg (76% based on CH acid compound used) of

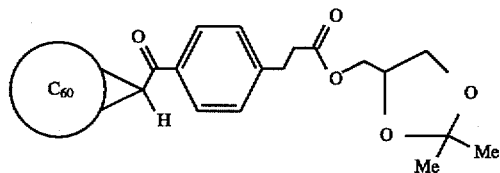

$R_f$ (SiO₂, toluene/MeOH 20:1)=0.68 MS (FAB): 1024 (M$^\ominus$, 50%), 720 (100%) ¹H-NMR (360 MHz, CDCl₃) δ=8.38 (d, J=8.3 Hz, 2 H), 7.50 (d, J=8.3 Hz, 2 H), 5.61 (s, 1 H), 4.29 (m, 1 H), 4.18, 4.10 (m, 2 H), 4.05, 3.69 (m, 2 H), 3.11 (t, J=7.5 Hz, 2 H), 2.78 (t, J=7.5 Hz, 2 ), 1.43 (s, 3 H), 1.37 (s, 3 H) ¹³C-NMR (100 MHz, CDCl₃) δ=189.18 (C=O), 172.15 (C=O), 146.66, 145.57, 145.38, 145.28, 145.18, 145.18, 145.07, 144.85, (1C), 144.73, 144.67, 144.64, 144.64, 144.62, 144.34, 143.93, 143.69, 143.32, 143.16 (1C), 143.03, 142.97 (1C), 142.97, 142.78, 142.47, 142.25, 142.21, 142.09, 141.20, 140.95, 139.58, 136.63, 134.24, 129.33, 129.28, 109.93, 73.56, 72.32, 66.26, 65.04, 44.16, 34.96, 30.92, 26.72, 25.37.

EXAMPLE 20

569 mg (0.79 mmol) of C₆₀ were stirred in 230 ml of toluene with 299 mg (0.73 mmol) of menthyl 3-[4-(2-bromoacetyl)phenyl]propionate and 113 mg (0.74 mmol) of DBU for 24 h. Chromatography: 150 g of silica gel (0.063–0.2 mm); 400 ml of toluene/i-hexane 1:1, 500 ml of toluene 186 mg of C₆₀ (33% based on C₆₀ used) recovered 423 mg (55% based on CH acid compound used) of

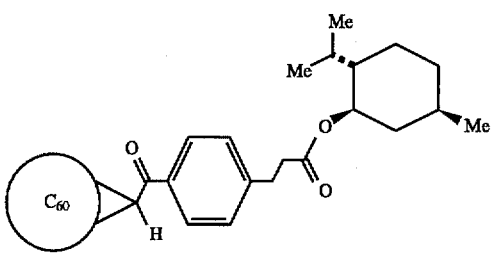

$R_f$ (SiO₂, toluene)=0.40 MS (FAB): 1048 (M$^\ominus$, 40%), 720 (80%) ¹H-NMR (360 MHz, CD₂Cl₂) δ=8.39 (d, J=8.3 Hz, 2 H), 7.53 (d, J=8.3 Hz, 2 H), 5.70 (s, 1 H), 4.69 (m, 1 H), 3.11 (t, J=7.5 Hz, 2 H), 2.72 (t, J=7.5 Hz, 2 H), 1.94 (m, 1 H), 1.75 (m, 1 H), 1.67 (m, 2 H), 1.51–1.21 (m, 3 H), 1.11–0.8 (m, 2 H), 0.91 (d, J=6.5 Hz, 3 H), 0.86 (d, J=7.0 Hz, 3 H), 0.72 (d, J=7.0 Hz, 3 H) ¹³C-NMR (100 MHz, CD₂Cl₂) δ=188.6 (C=O), 171.4 (C=O), 148.0, 147.9 (1C), 146.7, 145.3, 145.1, 144.9, 144.8, 144.8, 144.7, 144.5 (1C), 144.4, 144.3, 144.3, 144.2, 144.0, 143.6, 143.4, 142.9, 142.8 (1C), 142.7, 142.6, 142.6, 142.5, 142.2, 141.9, 141.8, 141.8, 140.8, 140.6, 139.2, 136.4 (1C), 136.4 (1C), 133.8 (1C), 129.0, 128.8, 74.0 (1C), 72.3 (2C), 46.8 (1C), 44.2, 40.6, 35.1, 33.9, 31.1, 30.8, 26.5, 23.1, 21.5, 20.3, 15.8

EXAMPLE 21

742 mg (1.03 mmol) of C₆₀ were stirred in 300 ml of toluene with 350 mg (0.91 mmol) of (6-hydroxyhexyl) 4-[4-(2-bromoacetyl)phenyl]butyrate and 139 mg (0.91 mmol) of DBU for 24 h. Chromatography: 150 g of silica gel (0.063–0.2 mm); 500 ml of methylene chloride/methane 100:1 to 100:3 359 mg of C₆₀ (48% based on C₆₀ used) recovered 536 mg (57% based on CH acid compound used) of

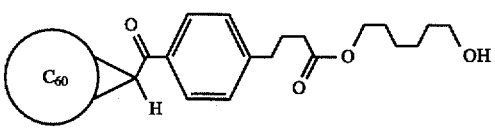

$R_f$ (SiO₂, CH₂Cl₂/MeOH 40/1)=0.36 MS (FAB): 1024 (M$^\ominus$, 50%), 734 (35%), 720 (100%) ¹H-NMR (360) MHz, CDCl₃): δ=8.38 (d, J=8.3 Hz, 2 H) 7.48 (d, J=8.3 Hz, 2 H), 5.62 (s, 1 H), 4.08 (t, J=6.7 Hz, 2 H), 3.63 (t, J=6.5 Hz, 2 H), 2.81 (t, J=7.6 Hz, 2 H), 2.37 (t, J=7.4 Hz, 2 H), 2.04 (quint, J=7.5 Hz, 2 H), 1.64 (m, 2 H), 1.57 (m, 2 H), 1.39 (m, 4 H) ¹³C-NMR (90) MHz, CDCl₃): δ=189.2 (C=O), 173.2 (C=O), 149.0 (1C), 148.1, 146.7, 145.6, 145.4, 145.3, 145.2, 145.2, 145.1, 144.9, (1C), 144.7, 144.7, 144.6, 144.6, 144.4, 143.9, 143.7, 143.3, 143.2 (1C), 143.0, 143.0, 143.0, 142.8, 142.5, 142.3, 142.2, 142.1, 141.2, 141.0, 139.6, 136.6, 136.6, 134.0, 129.5, 129.2, 72.4, 64.5, 62.8, 44.2, 35.3, 33.6, 32.6, 28.7, 26.1, 25.8, 25.4.

EXAMPLE 22

247 mg (0.34 mmol) of C₆₀ were stirred in 100 ml of toluene with 155 mg (0.33 mmol) of 3-[4-(2-bromoacetyl)-phenyl]-1-(1,4,7,10-tetraoxa-13-azacyclodec-13-yl) propan-1-one and 50 mg (0.33 mmol) of DBU for 24 h.

Chromatography:
a) 35 g of silica gel (0.063–0.2 mm); 100 ml of toluene, 315 ml of toluene/ethanol 100:5, 55 ml of toluene/ethanol 100:10, 100 ml of methylene chloride/ethanol 95:5 b) 25 g of silica gel (0.063–0.2 mm); 133 ml of toluene/ethanol 130:3, 132 ml of toluene/ethanol 130:2, 105 ml of toluene/ethanol 100:5, 52 ml of methylene chloride/ethanol 50:2, 105 ml of methylene chloride/ethanol 100:5

154 mg (42% based on CH acid compound used) of

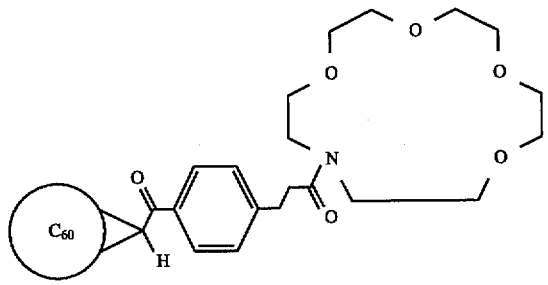

$R_f$ (SiO$_2$, toluene/methanol 20:1)=0.21 MS (FAB): 1112 (MH$^+$, 100%), 720 (85%) $^1$H-NMR (360 MHz, CD$_2$Cl$_2$) δ=8.40 (d, J=8.3 Hz, 2 H), 7.56 (d, J=8.2 Hz, 2 H), 5.72 (s, 1 H), 3.72 (t, J=6.6 Hz, 2 H), 3.64–3.53 (m, 16 H), 3.49 (t, J=6.6 Hz, 2 H), 3.12 (t, J=7.5 Hz, 2 H), 2.77 (t, J=7.5 Hz, 2 H) $^{13}$C-NMR (100 MHz, CDCl$_3$) δ=189.20 (C=O), 171.99 (C=O), 149.22 (1C), 148.11, 146.76, 145.60, 145.41, 145.28, 145.19, 145.17, 145.07, 144.87 (1C), 144.73, 144.67, 144.65, 144.63, 144.62, 144.34, 143.94, 143.70, 143.33, 143.16 (1C), 143.04, 142.98 (1C), 142.97, 142.78, 142.49, 142.26, 142.23, 142.10, 141.20, 140.95, 139.55, 136.62, 133.92, 129.51, 129.20, 72.40, 71.70, 70.68, 70.40, 70.20, 70.16, 70.14, 69.75, 69.64, 50.52, 49.56, 44.29, 34.24, 31.50

EXAMPLE 23

940 mg (1.3 mmol) of C$_{60}$ were stirred in 380 ml of toluene with 500 mg (1.27 mmol) of 4-nitrophenyl 3-[4-(2-bromoacetyl)phenyl]propionate and 194 mg (1.27 mmol) of DBU for 20 hours.

Chromatography: 180 g of silica gel (0.063–0.2 mm); 1600 ml of toluene 333 mg of C$_{60}$ (35% based on C$_{60}$ used) 704 mg (53% based on CH acid compound used) of

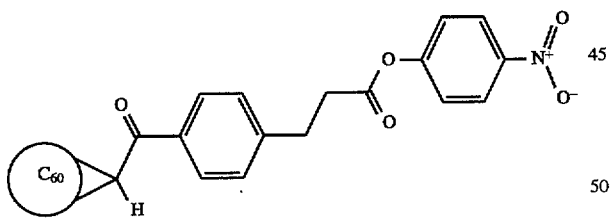

$R_f$ (SiO$_2$, toluene)=0.21 MS (FAB): 1031 (M$^\ominus$, 50%), 720 (100%) $^1$H (360 MHz, CDCl$_3$) δ=8.43 (d, J=8.3 Hz, 2 H), 8.25 (m, 2 H), 7.57 (d, J=8.1 Hz, 2 H), 1 signal for 2 aromatic protons is obscured by the toluene protons, 5.61 (s, 1 H), 3.24 (d, J=7.3 Hz, 2 H), 3.04 (d, J=7.3 Hz, 2 H)

EXAMPLE 24

1757 mg (2.44 mmol) of C$_{60}$ were stirred in 710 ml of toluene with 823 mg (2.03 mmol) of 4-nitrophenyl 4-[4-(2-bromoacetyl)phenyl]butyrate and 310 mg (2.03 mmol) of DBU for 7 h.

Chromatography: 400 g of silica gel (0.063–0.2 mm); 3500 ml of toluene 1128 mg (53% based on CH acid compound used) of

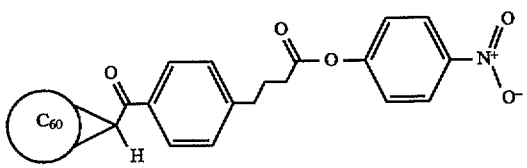

$R_f$ (SiO$_2$, toluene)=0.25 MS (FAB): 1045 (M$^\ominus$, 20%), 720 (100%) $^1$H-NMR (360 MHz, CD$_2$Cl$_2$) δ=8.43 (d, J=8.1 Hz, 2 H), 8.27 (d, J=9.0 Hz, 2 H), 7.56 (d, J=8.1 Hz, 2 H), 7.31 (d, J=9.0 Hz, 2 H), 5.72 (s, 1 H), 2.93 (t, J=7.6 Hz, 2 H), 2.71 (t, J=7.4 Hz, 2 H), 2.19 (quint, 7.6 Hz, 2 H) $^{13}$C-NMR (90 MHz, CDCl$_3$) δ=189.2, 170.7, 155.3 (1C), 148.3 (1C), 148.0, 146.7, 145.6, 145.4, 145.3, 145.2, 145.2, 145.1, 144.9 (1C), 144.8, 144.7, 144.7, 144.6, 144.6, 144.4, 143.9, 143.7, 143.3, 143.2 (1C), 143.1, 143.0, 143.0, 142.8, 142.5, 142.3, 142.2, 142.1, 141.2, 141.0, 139.6, 136.6, 134.2 (1C), 129.3, 129.3, 125.3, 122.3, 72.3, 44.2, 35.2, 33.5, 25.8.

EXAMPLE 25

471 mg (0.65 mmol) of C$_{60}$ were stirred in 200 ml of toluene with 168 mg (0.65 mmol) of 3-[4-(2-bromoacetyl)-phenyl]propan-1-ol and 100 mg (0.65 mmol) of DBU for 17 h.

Chromatography:

a) 80 g of silica gel (0.063–0.2 mm): 300 ml of toluene/methanol 100:1, 300 ml of toluene/methanol 30:1, 500 ml of toluene/methanol 25:1, 200 ml of toluene/methanol 20:1 b) 60 g of silica gel (0.063–0.2 mm); 900 ml of methylene chloride/methanol 100:1

290 mg (53% based on CH acid compound used) of

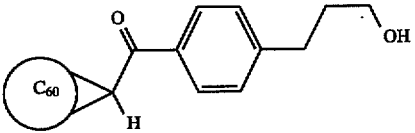

$R_f$ (SiO$_2$ CH$_2$Cl$_2$/MeOH 80:1)=0.25 MS (FAB): 896 (M$^\ominus$, 100%), 720 (90%) $^1$H-NMR (360 MHz, CDCl$_3$) δ=8.39 (d, J=8.3 Hz, 2 H), 7.50 (d, J=8.3 Hz, 2 H), 5.62 (s, 1 H), 3.73 (m, 2 H), 2.88 (t, J=7.7 Hz, 2 H, 1.98 (m, 2 H)

EXAMPLE 26

495 mg (0.65 mmol) of C$_{60}$ were stirred in 200 ml of toluene with 200 mg (0.58 mmol) of tert-butyl 4-[4-(2-bromo-2-chloroacetyl)phenyl]butyrate and 94 mg (0.62 mmol) of DBU for 17 h.

Chromatography: 200 g of silica gel (0.063–0.2 mm); 1000 ml of toluene 180 mg of C$_{60}$ (36% based on C$_{60}$ used) 370 mg (62% based on CH acid compound used) of

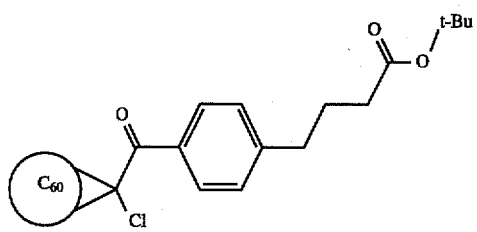

$R_f$ (SiO$_2$, toluene)=0.32 MS (FAB): 1014 (M$^\ominus$, 100%), 720 (50%)

EXAMPLE 27

74 mg (0.073 mmol) of the tert-butyl ester from Example 26 were dissolved in 10 ml of methylene chloride, and 148 mg (1.58 mmol) of methanesulfonic acid were added to this solution. After 2 minutes, 1 ml of water and 30 ml of methylene chloride were added. The organic phase was separated off and dried using magnesium sulfate.

Chromatography: 15 g of silica gel (0.063–0.1 mm); 140 ml of methylene chloride/acetic acid 40:1 37.7 mg (53%) of

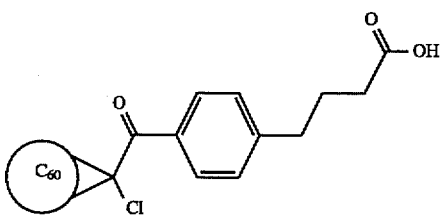

$R_f$(SiO$_2$, CH$_2$Cl$_2$/AcOH 20:0.5)=0.36 MS (FAB): 958 (M$^\ominus$, 100%), 720 (70%)

EXAMPLE 28

100 mg (0.11 mmol) of the alcohol from Example 25 were suspended in 30 ml of methylene chloride, 89 mg (0.89 mmol) of succinic anhydride and 27 mg (0.22 mmol) of DMAP were added and the reaction mixture was stirred for 1 week at room temperature. One drop of concentrated hydrochloric acid was added to the reaction mixture and the latter was dried using magnesium sulfate.

Chromatography: 50 g of silica gel (0.063–0.2 mm); 800 ml of methylene chloride/methanol 200:1, 800 ml of methylene chloride 200:3 56 mg (50%) of

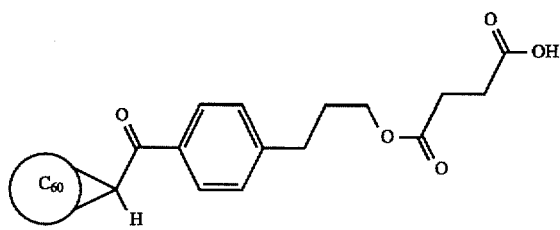

$R_f$(SiO$_2$, CH$_2$Cl$_2$/MeOH 20:1)=0.08 MS (FAB): 997 (MH$^\oplus$, 25%), 720 (100%)

EXAMPLE 29

A solution of 19 mg (0.018 mmol) of the p-nitrophenyl ester from Example 23 in 18 ml of toluene was stirred at room temperature with 2.0 mg (0.018 mmol) of benzylamine for 12 days.

Chromatography: 5 g of silica gel (0.063–0.2 mm); 50 ml of methylene chloride, 52 ml of methylene chloride/methanol 25:1 9.5 mg (51%) of

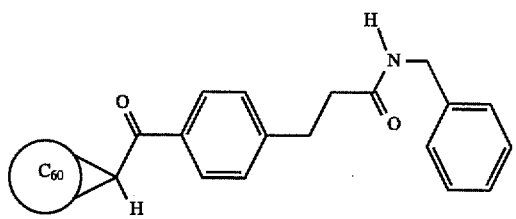

$R_f$ (SiO$_2$, CH$_2$Cl$_2$)=0.07 MS (FAB): 999 (M$^\ominus$, 70%), 720 (100%)

EXAMPLE 30

A solution of 50 mg (0.048 mmol) of the p-nitrophenyl ester from Example 23 in 75 ml of toluene was stirred at room temperature with 20 mg (0.16mmol) of glycine methyl ester hydrochloride and 16 mg (0.16 mmol) of triethylamine for 10 days. The reaction mixture was filtered and chromatographed.

Chromatography:

a) 30 g of silica gel (0.063–0.2 mm); 101 ml of methylene chloride/methanol 100:1, 102 ml of methylene chloride/methanol 100:2, 103 ml of methylene chloride/methanol 100:3, 180 ml of methylene chloride/methanol/triethylamine 20:1.5:1 b) 12 g of silica gel (0.063–0.2 mm); 123 ml of methylene chloride/methanol 100: 2.5

35 mg (75%) of

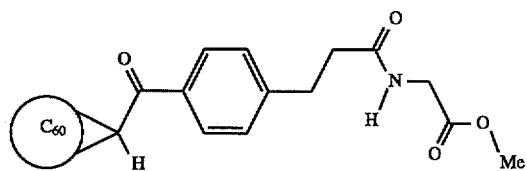

$R_f$(SiO$_2$, CH$_2$Cl$_2$/MeOH 40:1)=0.33 MS (FAB): 981 (M$^\ominus$) $^1$H-NMR (360 MHz, CDCl$_3$) δ=8.38 (d, J=8.3 Hz, 2 H), 7.51 (d, J=8.3 Hz, 2 H), 5.61 (s, 1 H), 4.04 (m, 2 H), 3.75 (s, 3 H), 3.14 (t, J=7.6 Hz, 2 H), 2.64 (t, J=7.6 Hz, 2 H).

EXAMPLE 31

A solution of 100 mg (0.097 mmol) of the p-nitrophenyl ester from Example 23 in 40 ml of toluene was stirred at room temperature with 9.9 mg (0.097 mmol) of 1,3-bis-(methylamino)propane. 100 mg (1.8 mmol) of methyl isocyanate were added to the reaction mixture and this mixture was stirred for 6 days at room temperature. The reaction mixture was filtered and chromatographed.

Chromatography:

a) 50 g of silica gel (0.063–0.2 mm); 410 ml of methylene chloride/methanol 200:5, 210 ml of methylene chloride/methanol 100:5

43 mg (42%) of

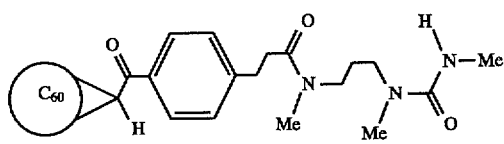

$R_f$(SiO$_2$, CH$_2$Cl$_2$/MeOH 20:1)=0.13 MS (FAB): 1051 (M$^\ominus$)

EXAMPLE 32

The procedure of Example 3 was repeated, with 59 mg (0.082 mmol) of C$_{60}$ in 25 ml of toluene being reacted with 20.7 mg (0.163 mmol) of iodine, 22.4 mg (0.082 mmol) of tetraethyl methylenebisphosphonate and 24.9 mg of DBU. After a reaction time of 3 days at room temperature, the reaction mixture was filtered and chromatographed on 30 g of silica gel (0.063–0.2 mm). C$_{60}$ was eluted with toluene and the monoaddition product was eluted with 150 ml of methylene chloride/ethanol 20:1. This gave 8 mg (9% based on C$_{60}$ used) of monoaddition product.

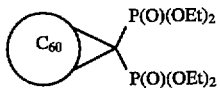

$R_f$(SiO$_2$, CH$_2$Cl$_2$/EtOH 20:1)=0.4 MS (FAB): 1006 (M$^\ominus$, 50%), 720 (100%)

EXAMPLE 33

The procedure of Example 3 was repeated, with 59 mg (0.082 mmol) of C$_{60}$ in 25 ml of toluene being reacted with 20.7 mg (0.163 mmol) of iodine, 8.1 mg (0.082 mmol) of acetylacetone and 24.9 mg of DBU. After a reaction time of 3 days at room temperature, the reaction mixture was filtered and chromatographed over 40 g of silica gel (0.063–0.2 mm). C$_{60}$ was eluted with 100 ml of toluene/i-hexane 1:1 and the monoaddition product was eluted with 250 ml of toluene/i-hexane 2:1. This gave 12 mg (17% based on C60 used) of monoaddition product.

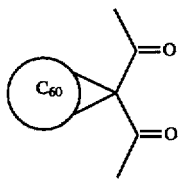

$R_f$(SiO$_2$, toluene)=0.4 MS (FAB): 818 (M$^\ominus$, 100%), 720 (100%) $^1$H-NMR (360 MHz, CDCl$_3$): δ=2.82 (s).

EXAMPLE 34

51 mg (0.299 mmol) of C$_{70}$ in 200 ml of toluene were placed in a 250 ml nitrogen flask which had been evacuated and flushed with argon, and 55 mg (0.230 mmol) of diethyl bromomalonate and 35.8 mg (0.235 mmol) of DBU were injected into the suspension. After stirring for 4 h at room temperature, the suspension was filtered and the clear solution was evaporated to about 75 ml. According to HPLC, 60% of the C$_{70}$ used were reacted. After chromatography over SiO$_2$ (0.063–0.2 nun) using toluene/i-hexane and toluene, 110 mg of C$_{70}$ (43% based on C$_{70}$ used) were recovered and

was obtained in microcrystalline form (138 mg, 60% based on bromomalonate). $R_f$(SiO$_2$, toluene)=0.47 MS (FAB): 998 (M$^\ominus$) $^1$H-NMR (360 MHz, CDCl$_3$): δ=4.50 (m, 4 H), 1.46 (t, J=7.1 Hz, 6 H). $^{13}$C-NMR (100 MHz, CDCl$_3$): δ=163.45, 155.12, 151.38 (3C), 151.19, 150.74, 150.60, 149.36, 149.27, 149.12, 148.72, 148.59, 148.53, 148.49, 147.67, 147.54, 147.32, 147.02, 146.47 (1C), 145.95, 145.93, 144.89; 143.96, 143.86, 143.54, 142.95, 142.85, 142.25, 141.68, 140.81, 136.98, 133.59, 132.84, 130.95, 130.91, 130.83, 66.90, 66.24, 63.47, 37.22, 14.23. Analysis calc. for C$_{77}$H$_{10}$O$_4$: C: 92.6% H: 1.0% found C: 93.7% H: 0.9%

EXAMPLE 35

The procedure of Example 34 was repeated, with 250 mg (0.3 mmol) of C$_{70}$ in 250 ml of toluene being reacted with 66 mg (0.31 mmol) of dimethyl bromomalonate and 48 mg (0.31 mmol) of DBU. After stirring for 3 h at room temperature, the suspension was filtered and the clear brownish violet solution was evaporated to about 60 ml and chromatographed over SiO$_2$ (0.063–0.2 mm) using toluene/ i-hexane 1:1 to 3:1 and toluene. 42 mg of C$_{70}$ (16.8%) were recovered and

was obtained in microcrystalline form (137 mg, 47%). $R_f$ (SiO$_2$, toluene)=0.36 MS (FAB): 970 (M$^\ominus$, 70%), 840 (100%) $^1$H-NMR (360 MHz, CDCl$_3$/CS$_2$): δ=4.02 (s) $^{13}$C-NMR (100 MHz, CDCl$_3$/CS$_2$): δ=163.29, 154.77, 151.19, 151.12 (1C), 150.94, 150.48, 150.35, 149.12, 149.03, 148.91, 148.54, 148.37, 148.30, 148.26, 147.38, 147.30, 147.10, 146.78, 146.14 (1C), 145.77, 145.71, 144.63, 143.77, 143.66, 143.38, 142.67, 142.56, 142.05, 141.45, 140.62, 136.64, 133.36, 132.59, 130.73 (4C), 130.60, 53.72: owing to a poor signal-to-noise ratio: no signals for the cyclopropane ring.

EXAMPLE 36

The procedure of Example 34 was repeated, with 251 mg (0.299 mmol) of C$_{70}$ in 250 ml of toluene being reacted with 139 mg (0.3 mmol) of didecyl bromomalonate and 45.6 mg (0.3 mmol) of DBU. After a reaction time of 4 h at room temperature, the reaction mixture was filtered, the solvent was removed and the residue was extracted with diethyl ether. The ether solution was filtered through a short silica gel column and the solvent was removed.

The residue was dissolved in about 5 ml of i-hexane/-toluene 2:1 and chromatographed over 250 g of silica gel (0.063–0.2 mm) using 2.2 l of i-hexane/toluene 2:1 and 1.1 l of i-hexane/toluene 1:2.

This gave 129 mg (35% based on C$_{70}$ used) of monoadduct

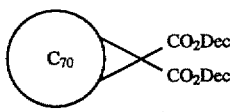

and also 95 mg (19%) of diadduct as a mixture of isomers. $R_f$(SiO$_2$; toluene/i-hexane 1:2)=0.18 MS (FAB): 1222 (M$^\ominus$, 60%), 840 (100%) $^1$H-NMR (360 MHz, CDCl$_3$): δ=4.42 (t, J=6.5 Hz, 4H), 1.81 (m, 4H), 1.46 (m, 4H), 1.25 (m, 24H), 0.86 (s, 6H) $^{13}$C-NMR (100 MHz, CDCl$_3$): δ=163.51, 155.06, 151.35, 51.32 (1C), 151.14, 150.69, 150.55, 149.31, 149.22, 49.08, 148.67, 148.53, 148.48, 148.45, 147.61, 147.49, 147.27, 146.97, 146.42 (1C), 145.90, 145.88, 144.82, 143.91, 143.81, 143.49, 142.94, 142.79, 142.17, 141.62, 140.72, 136.98, 133.54, 132.79, 130.89, 130.85, 130.77, 67.52(2C), 66.91(1C), 66.24(1C), 37.39(1C), 31.89, 29.63, 29.57, 29.34, 29.25, 28.58, 26.02, 22.69, 14.12.

EXAMPLE 37

The procedure of Example 34 was repeated, with 250 mg (0.3 mmol) of C$_{70}$ in 250 ml of toluene being reacted with 139 mg (0.3 mmol) of di(2-(2-methoxyethoxy)ethyl) bromomalonate and 45.6 mg (0.3 mmol) of DBU. After a reaction time of 6 hours at room temperature (75% conversion of the C$_{70}$ used according to HPLC), the reaction mixture was filtered and chromatographed over 45 g of silica gel (0.063–0.2 mm). C$_{70}$ was eluted with toluene and the addition products were eluted with 800 ml of toluene/diethyl ether 1:1 and 400 ml of toluene/ethanol 9:1. This gave 75 mg (14%) of C$_{70}$, 139 mg (40%) of monoadduct

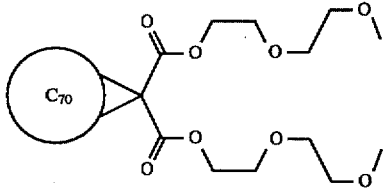

and 96 mg (22%) of diadduct as a mixture of isomers. $R_f$(SiO$_2$; toluene/diethyl ether 1:1)=0.25 MS (FAB): 1146 (M$^\ominus$, 55%), 840 (100%) $^1$H-NMR (360 MHz, CDCl$_3$): δ=4.59 (m, 4H), 3.85 (m, 4H), 3.68 (m, 4H), 3.54 (m, 4H), 3.37 (s, 6H).

EXAMPLE 38

The procedure of Example 34 was repeated, with 251 mg (0.3 mmol) of C$_{70}$ being suspended in 250 ml of toluene and reacted with 75 mg (0.45 mmol) of ethyl 2-chloroacetate and 60 mg (0.39 mmol) of DBU. After a reaction time of 24 h at room temperature, the reaction mixture was filtered, the conversion was determined as 64% by HPLC and the solution was evaporated to about 60 ml. Chromatography over SiO$_2$ (0.063–0.2 mm) using toluene/i-hexane 1:1 to 4:1 gave 104 mg (35.7%) of

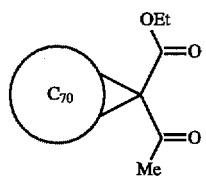

$R_f$ (SiO$_2$, toluene)=0.38. MS (FAB): 968 (M$^-$). $^1$H-NMR (360 MHz, CDCl$_3$): δ=4.52 (m, 2H), 2.82 (s, 3H), 1.48 (t, J=7.1 Hz, 3H).

EXAMPLE 39

The procedure of Example 34 was repeated, with 250 mg (0.3 mmol) of C$_{70}$ in 250 ml of toluene being reacted with 75 mg (0.37 mmol) of ω-bromoacetophenone and 50.2 mg (0.37 mmol) of DBU. After a reaction time of 22 h at room temperature (56% conversion of the C$_{70}$ used according to HPLC), the reaction mixture was filtered and the reaction solution was evaporated to 70 ml. Chromatography over 250 g of silica gel (0.063–0.2 mm) using toluene/i-hexane 1:3, 1:2 and 1:1, carried out three times, gave 58.2 mg (20%) of monoadduct.

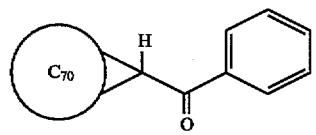

$R_f$(SiO$_2$; toluene/i-hexane 1:2)=0.12 MS (FAB): 958 (M$^-$, 70%), 840 (100%) $^1$H-NMR (360 MHz, CDCl$_3$): δ=8.42 (m, 2 H$_{ortho}$) 7.76 (m, 1 H$_{para}$), 7.68 (m, 2 H$_{meta}$), 4.42 (S, 3H).

EXAMPLE 40

The procedure of Example 34 was repeated, with 200 mg (0.24 mmol) of C$_{70}$ in 200 ml of toluene being reacted with 62.5 g (0.2 mmol) of ethyl 4-[4-(2-bromoacetyl)-phenyl] butyrate and 30.5 mg (0.2 mmol) of DBU. After a reaction time of 24 h at room temperature, 3 drops of 1 molar sulfuric acid were added, the mixture was dried with magnesium sulfate and filtered. The solution was evaporated to 80 ml and chromatographed over 80 g of silica gel (0.063–0.2 nun) using 600 ml of toluene. This gave 110 mg (55% based on C$_{70}$ used) of C$_{70}$ and 34 mg (16% based on C$_{70}$ used and 29% based on C$_{70}$ reacted) of monoadduct.

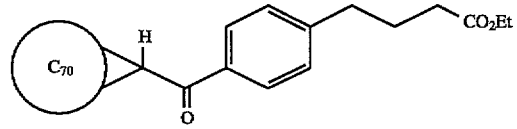

$R_f$(SiO$_2$; toluene)=0.27 MS (FAB): 1072 (M$^\ominus$, 50%), 840 (100%). $^1$H-NMR (360 MHz, CD$_2$Cl$_2$): δ=8.36 (d, J=8.3 Hz, 2H), 7.52 (d, J=8.3 Hz, 2H), 4.50 (s, 1H), 4.13 (m, 2H), 2.84 (t, J=7.7 Hz, 2H), 2.39 (t, J=7.4 Hz, 2H), 2.04 (quint, J=7.5 Hz, 2H), 1.26 (t, J=7.1 Hz, 3H).

I claim:
1. A fullerene derivative of the formula I

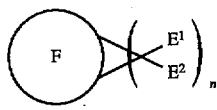

where the symbols and indices have the following meanings:
F: is a fullerene radical of the formula $C_{(20+2m)}$ where m=20, 25, 28, 29;
$E^1$, $E^2$: are identical or different and are each COOH, COOR, CONRR$^1$, CHO, COR, CN, P(O)(OR)$_2$ and SO$_2$R, where R, R$^1$ are each a straight-chain or branched, aliphatic radical (C$_1$ to C$_{20}$) which may be unsubstituted or monosubstituted or polysubstituted by identical or different substituents, in which radical up to every third CH$_2$ unit can be replaced by O or NR$^4$, where R$^4$ is (C$_1$–C$_{20}$)-alkyl or benzyl, or a benzyl radical or phenyl radical which can be unsubstituted or substituted by from 1 to 5 substituents R, OH, OR, COOR, OCOR, SO$_3$H, SO$_2$Cl, F, Cl, Br, NO$_2$ and CN or together are

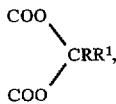

or are different from one another and are each COR, R or H, or are different from one another and are each COR/R or F/Cl/Br, where R is as defined above, or are different from one another and are each NO$_2$, R$^3$ or H, where R$^3$ is an unsubstituted, monosubstituted or polysubstituted aliphatic radical (C$_1$ to C$_{20}$);
n: is a natural number from 1 to 10+m where m=20, 25, 28, 29.

2. A fullerene derivative of the formula I as claimed in claim 1, where the symbols and indices have the following meanings:
F: is a fullerene radical of the formula $C_{(20+2m)}$ where m=20, 25, 28, 29,
$E^1$, $E^2$: are identical or different and are each COOR, COR, P(O)(OR)$_2$, COOH, CN, where R is a straight-chain or branched, aliphatic radical (C$_1$ to C$_{20}$) which may be unsubstituted or monosubstituted or polysubstituted by identical or different substituents, in which radical up to every third CH$_2$ unit can be replaced by O or NR$^4$, where R$^4$=(C$_1$–C$_{20}$)-alkyl or benzyl, or a benzyl radical or phenyl radical which can be unsubstituted or substituted by from 1 to 3 substituents R, OH, OR, COOR, OCOR, SO$_3$H, SO$_2$Cl, F, Cl, Br, NO$_2$ and CN, or together are

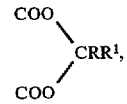

or are different from one another and are each COR, R or H, or are different from one another and are each COR/R or F/Cl/Br,
n: is a natural number from 1 to 12.

3. A fullerene derivative of the formula I as claimed in claim 1, where the symbols and indices have the following meanings:

R: C$_{60}$, C$_{70}$
E1/E2: CO$_2$R$^1$/CO$_2$R$^2$; CO$_2$R$^1$/COR$^2$; CO$_2$R$^1$/CN; COAr/R$^1$ or H; COAr/R$^1$ or Cl;

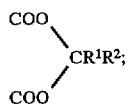

COR$^1$/COR$^2$; P(O)(OR$^1$)$_2$/P(O)(OR$^2$)$_2$; COOH/COOH;

where R$^1$ and R$^2$ are identical or different and are each a straight-chain or branched alkyl radical (C$_1$ to C$_{20}$) which may be unsubstituted or monosubstituted or polysubstituted by identical or different substituents, in which radical every third CH$_2$ unit can be replaced by O or NR$^4$, where R$^4$= (C$_1$–C$_{20}$)-alkyl or benzyl, or a benzyl radical or phenyl radical which can be unsubstituted or substituted by from 1 to 3 substituents OH, OMe, CO$_2$R$^1$, OOCR$^1$, SO$_3$H, SO$_2$Cl, F, Cl, Br, NO$_2$ and CN, and Ar is a phenyl radical which can likewise be substituted by from 1 to 3 substituents OH, OMe, Me, CO$_2$R$^1$, OCOR$^1$, SO$_3$H, SO$_2$Cl, F, Cl, Br, NO$_2$ and CN or can be substituted by a straight-chain or branched aliphatic radical (C$_1$–C$_{20}$), preferably C$_1$–C$_{10}$, which may be unsubstituted or monosubstituted or disubstituted by identical or different substituents COOR$^5$, CONHR$^5$, CONR$_2^5$, CONH$_2$, CONR$^6$, COOH, OH or OCOR$^5$, COOAr, COOCH$_2$Ar, where R$^5$=

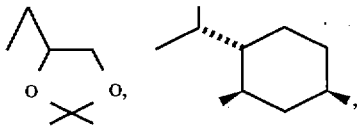

C$_1$–C$_6$-alkyl, hydroxy- (C$_1$–C$_6$)-alkyl, carboxy (C$_1$–C$_6$)-alkyl or (C$_1$–C$_3$)-alkylcarboxyl (C$_1$–C$_6$)-alkyl;
R$^6$=C$_{11}$–C$_{17}$-alkylene in which up to every 3rd CH$_2$ unit can be replaced by O and which together with the amide nitrogen forms a C$_{12}$–C$_{18}$ ring, and Ar is as defined above;
n: is a natural number from 1 to 6.

4. A fullerene derivative of the formula I as claimed in claim 1, where the symbols and indices have the following meanings:
F: C$_{60}$, C$_{70}$
E$^1$/E$^2$: CO$_2$Alkyl$^1$/CO$_2$Alkyl$^1$; CO$_2$Alkyl$^1$/COAlkyl$^2$; COAr/Ar; COAr;Alkyl$^1$; COAr/H where Alkyl$^1$, Alkyl$^2$ are each a straight-chain or branched alkyl radical having from 1 to 10 carbon atoms in which up to every third CH$_2$ unit can be replaced by O, and Ar is a phenyl group which can be substituted by a straight-chain or branched aliphatic radical (C$_1$–C$_6$) which may be unsubstituted or monosubstituted or disubstituted by identical or different substituents COOR$^5$, CONHR$^5$, CONR$_2^5$, CONR$^6$, COOH, OH or OCOR$^5$, where R$^5$ and R$^6$ are as defined above,
n: is 1 or 2.

5. A process for preparing fullerene derivatives as claimed in claim 1, which comprises reacting a fullerene of the formula C$_{(20+2m)}$ (m=a natural number) in an aprotic organic solvent with a CH acid component of the formula II

 II where the symbols and indices have the following meanings

F is a fullerene radical of the formula $C_{(20+2m)}$ where m=20, 25, 28, 29, $E^1$ and $E^2$ are identical or different and are each COOH, COOR, $CONRR^1$, CHO, COR, CN, $P(O)(OR)_2$ and $SO_2R$, where R, $R^1$ are each a straight-chain or branched aliphatic radical ($C_1$ to $C_{20}$) which may be unsubstituted or monosubstituted or polysubstituted by identical or different substituents, in which radical up to every third $CH_2$ unit can be replaced by O or $NR^4$, where $R^4$ is ($C_1$–$C_{20}$)-alkyl or benzyl, or a benzyl radical or phenyl radical which can be unsubstituted or substituted by from 1 to 5 substituents R, OH, OR, COOR, OCOR, $SO_3H$, $SO_2Cl$, F, Cl, Br, $NO_2$ and CN or together are

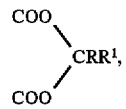

or are different from one another and are each COR, R or H, or are different from one another and are each COR/R or F/Cl/Br, or are different from one another and are each $NO_2$, $R^3$ or H, where $R^3$ can be an unsubstituted, monosubstituted or polysubstituted aliphatic radical ($C_1$ to $C_{20}$), X is —Cl, —Br, —I, —$OSO_2Ar$, $OSO_2CF_3$, $OSO_2C_4F_9$, and alkali metal hydrides, alkali metal hydroxides, alkoxides, amides, amines or guanidines in a temperature range from −78° C. to 180° C.

* * * * *